United States Patent [19]
Pfäffli et al.

[11] 4,301,290
[45] Nov. 17, 1981

[54] ORGANIC COMPOUNDS

[75] Inventors: Paul Pfäffli, Oberwil; Hartmut Hauth, Riehen, both of Switzerland

[73] Assignee: Sandoz Ltd., Basel, Switzerland

[21] Appl. No.: 18,439

[22] Filed: Mar. 7, 1979

Related U.S. Application Data

[63] Continuation-in-part of Ser. No. 944,487, Sep. 21, 1978, abandoned, which is a continuation-in-part of Ser. No. 914,707, Jun. 12, 1978, abandoned, which is a continuation-in-part of Ser. No. 749,349, Dec. 10, 1976, abandoned.

[30] Foreign Application Priority Data

| Dec. 16, 1975 | [CH] | Switzerland | 16283/75 |
| Dec. 16, 1975 | [CH] | Switzerland | 16284/75 |
| Sep. 22, 1977 | [CH] | Switzerland | 11599/77 |
| Mar. 10, 1978 | [CH] | Switzerland | 2643/78 |
| May 12, 1978 | [CH] | Switzerland | 5205/78 |
| Jun. 8, 1978 | [CH] | Switzerland | 6283/78 |

[51] Int. Cl.³ .............. C07D 217/14; C07D 217/16; A61K 31/47
[52] U.S. Cl. .................. 546/143; 546/144; 424/258
[58] Field of Search ............... 546/144, 143

[56] References Cited

U.S. PATENT DOCUMENTS

| 3,880,862 | 4/1975 | Meltzer | 546/46 |
| 4,150,135 | 4/1979 | Ripka | 546/144 |

FOREIGN PATENT DOCUMENTS 802587 11/1974 Belgium .

*Primary Examiner*—Donald G. Daus
*Assistant Examiner*—W. B. Springer
*Attorney, Agent, or Firm*—Gerald D. Sharkin; Robert S. Honor; Timothy G. Rothwell

[57] ABSTRACT

Decahydro or octahydro-4-phenyl-cis-isoquinoline derivatives are useful as analgesics, anti-depressants, tranquilizers and sleep inducers.

24 Claims, No Drawings

ORGANIC COMPOUNDS

This is a continuation-in-part of our application No. 944,487 of Sept. 21, 1979 now abandoned which in turn is a continuation-in-part of our application No. 914,707 of June 12, 1978 now abandoned which in turn is a continuation in-part of our application No. 749,349 of Dec. 10, 1976 now abandoned.

The present invention relates to cis-4a-phenylisoquinolines.

The present invention provides compounds of formula I,

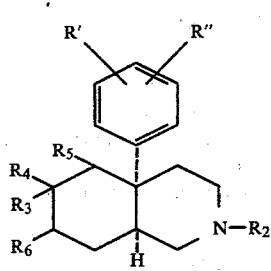

wherein either
(A) R′ is $OR_1$ wherein
$R_1$ is as defined hereinafter and
R″ is hydrogen, and
(i) $R_1$ is hydrogen or alkyl of 1 to 4 carbon atoms,
$R_2$ is hydrogen,
$R_3$ and $R_4$ together are oxygen, and each of $R_5$ and $R_6$ is hydrogen, or
(ii) $R_1$ is hydrogen, alkyl of 1 to 4 carbon atoms, or alkanoyl of 1 to 4 carbon atoms, and
$R_2$ is alkyl of 1 to 6 carbon atoms, a radical of formula II,

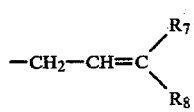

wherein
$R_7$ and $R_8$ are, independently, hydrogen or alkyl of 1 to 4 carbon atoms,
a radical of formula III,

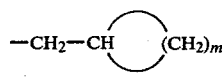

wherein
m is a whole number from 2 to 4,
a radical of formula IV,

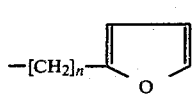

wherein
n is 1 or 2, or a radical of formula V,

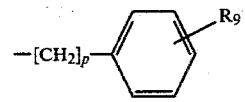

wherein
p is 1 or 2, and
$R_9$ is hydrogen, halogen, trifluoromethyl, lower alkoxy or lower alkyl, amino, or di(lower alkyl)amino, and
(a) either $R_3$ is azido or hydroxy, and
$R_4$ is hydrogen, or
$R_3$ and $R_4$, together, are oxygen, or methylene, and each of $R_5$ and $R_6$ is hydrogen, or
(b) either $R_3$ and $R_6$, together, form a bond, and each of $R_4$ and $R_5$ is hydrogen, or $R_4$ and $R_5$, together, form a bond, and each of $R_3$ and $R_6$ is hydrogen, with the proviso that when $R_3$ is hydroxy and $R_4$ is hydrogen, or when $R_3$ and $R_4$, together, are oxygen, and
(i) when $R_2$ is a radical of formula IV, then n is 1, or
(ii) when $R_2$ is a radical of formula V, then p is 2, and $R_9$ is hydrogen or halogen, or
(B) R′ and R″ are, independently, hydrogen, alkyl of 1 to 6 carbon atoms, trifluoromethyl, halogen or alkoxy of 1 to 4 carbon atoms, with the proviso that when R′ is alkoxy R″ is other than hydrogen,
$R_2$ is alkyl of 1 to 6 carbon atoms, a radical of formula II,

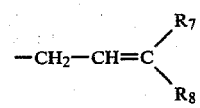

wherein
$R_7$ and $R_8$ are, independently, hydrogen or alkyl of 1 to 4 carbon atoms,
a radical of formula III,

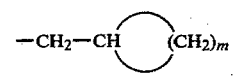

wherein
m is a whole number from 2 to 4,
a radical of formula IV,

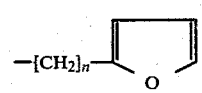

wherein
n is 1 or 2, or a radical of formula V,

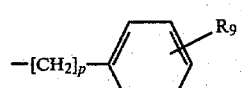

wherein
p is 1 or 2, and $R_9$ is hydrogen, halogen, trifluoromethyl, lower alkoxy or lower alkyl, amino, or di(lower alkyl)amino, or alkylamino ($C_{1-4}$), $R_3$ is azido, and $R_4$, $R_5$ and $R_6$ are hydrogen, or (C) R' and R" are, independently, hydrogen, alkyl of 1 to 6 carbon atoms, trifluoromethyl, halogen or alkoxy of 1 to 4 carbon atoms, $R_2$ is hydrogen, $R_3$ is azido and $R_4$, $R_5$ and $R_6$ are hydrogen.

Any lower alkyl or alkoxy radical, except where otherwise indicated hereinafter, preferably has 2, or especially one carbon atom.

When $R_1$ is alkanoyl, this preferably is formyl or especially acetyl. The radical $OR_1$ is preferably in the meta position.

$R_1$ is preferably hydrogen.

When $R_2$ is alkyl, this preferably has 1 to 4 carbon atoms, and especially 1 or 2 carbon atoms. $R_7$ and $R_8$ are preferably identical and are conveniently both hydrogen. m is preferably 2 or 3. n is preferably 1. p is preferably 2. $R_9$ is preferably in the para position or, when $R_9$ is halogen, in the ortho position. $R_9$ is conveniently hydrogen or halogen. Halogen means fluorine, chlorine or bromine. The halogen atom is preferably fluorine or chlorine.

$R_2$ is preferably alkyl.

When $R_3$ is azido or hydroxy and $R_4$ is hydrogen, $R_3$ may be cis or trans to the phenyl group in the 4-position.

Preferably $R_3$ and $R_4$ are together oxygen. Alternatively, preferably $R_3$ is azido and $R_4$ is hydrogen.

$R_9$ is conveniently other than alkylamino. R' and R" are conveniently other than halogen. R' is conveniently in the meta-position. R" is conveniently hydrogen. In groups (B) and (C) R' is conveniently alkoxy or hydrogen.

The present invention provides a process for the production of a compound of formula I, which comprises (a) splitting off the amino protecting group $R_{10}$ present in a compound of formula VI,

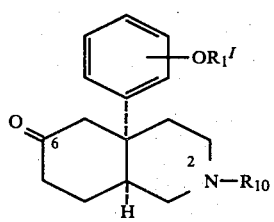

VI wherein $R_1^I$ is hydrogen or alkyl of 1 to 4 carbon atoms, and $R_{10}$ is an amino protecting group, to produce a compound of formula Ia,

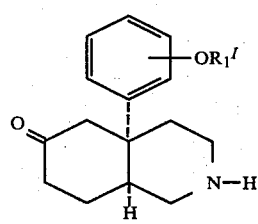

Ia wherein $R_1^I$ is as defined above, (b) alkylating a compound of formula Ia, as defined above, or the corresponding compound wherein the keto group is protected, and if necessary splitting off any keto protecting group in the resultant product, to produce a compound of formula Ib,

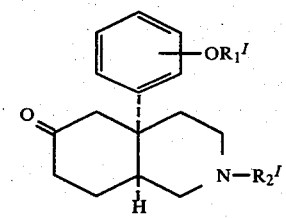

Ib wherein $R_1^I$ is as defined above, and $R_2^I$ is $R_2$ as defined above, with the proviso that it is other than hydrogen, (c) reducing a compound of formula Ic,

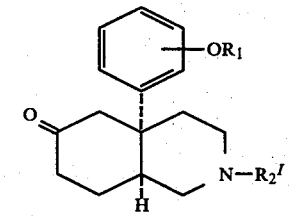

Ic wherein $R_1$ and $R_2^I$ are as defined above, to produce a compound of formula Id,

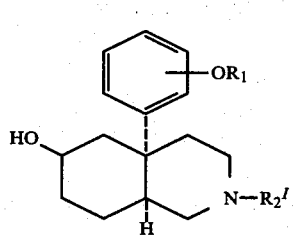

Id wherein $R_1$ and $R_2^I$ are as defined above, (d) replacing a leaving group $R_{11}$ by azido in a compound of formula VII,

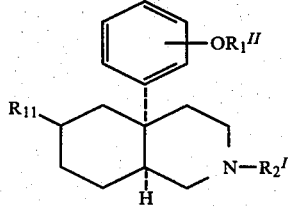

VII wherein $R_1^{II}$ is alkyl of 1 to 4 carbon atoms or alkanoyl of 1 to 4 carbon atoms, $R_2^I$ is as defined above, and $R_{11}$ is a leaving group, to produce a compound of formula Ie,

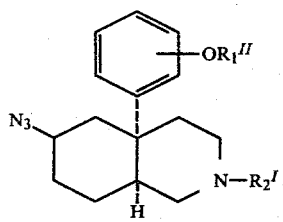

wherein
$R_1^{II}$ and $R_2^I$ is as defined above, (e) eliminating $HR_{11}$ from a compound of formula VIII,

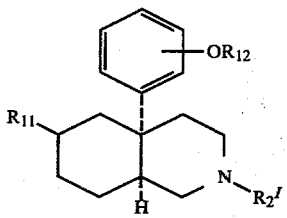

wherein
$R_{11}$ and $R_2^I$ are as defined above, and
$R_{12}$ is a group capable of being split off under the reaction conditions, alkyl of 1 to 4 carbon atoms, or alkanoyl of 1 to 4 carbon atoms, to form a compound of formula If,

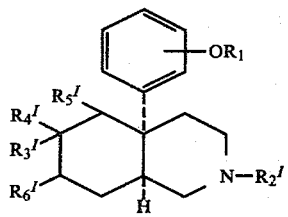

wherein
$R_1$ and $R_2^I$ are as defined above, and either
$R_3^I$ and $R_6^I$, together, form a bond, and each of $R_4^I$ and $R_5^I$ is hydrogen, or
$R_4^I$ and $R_5^I$, together, form a bond, and each of $R_3^I$ and $R_6^I$ is hydrogen, (f) splitting off a hydroxy protecting group $R_{13}$ from a compound of formula IX,

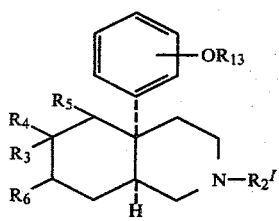

wherein
$R_2^I$, $R_3$, $R_4$, $R_5$ and $R_6$ are as defined above, with the proviso that when $R_3$ and $R_4$ are together oxygen, the keto group may be in free form or protected form, and $R_{13}$ is a hydroxy protecting group, to produce a compound of formula I, wherein $R_1$ is hydrogen, (g) acylating a compound of formula I, wherein $R_1$ is hyrogen, and $R_2$ is $R_2^I$ as defined above to produce a compound of formula I, wherein $R_1$ is alkanoyl of 1 to 4 carbon atoms, or (h) replacing the oxygen of the keto group of a compound of formula Ic by methylene under Wittig conditions to form a compound of formula Ig,

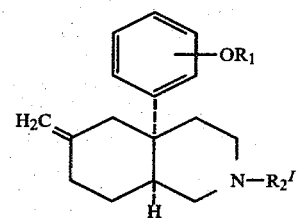

wherein
$R_1$ is as defined above in connection with formula I, and
$R_2^I$ is as defined above.

Alternatively compounds of groups (B) and (C) may be made in analogous manner, e.g. by (a') splitting off a benzoyl group from a compound of formula XIII

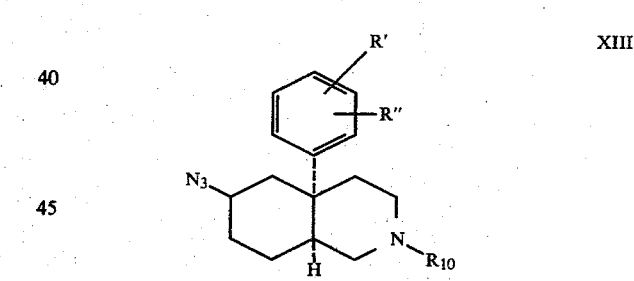

wherein R' and R" are as defined above under group (B) or (C), and $R_{10}$ is as defined above to produce a compound of formula I'a

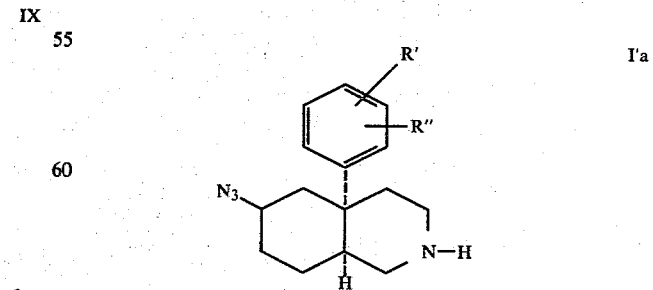

or (b') alkylating a compound of formula I'a to produce a compound of formula I'b

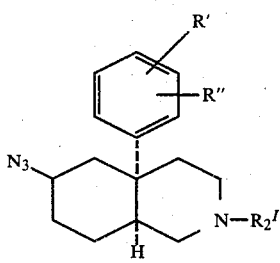

I'b wherein R' and R" are as defined above under group (B) or (C), and $R'_2$ is as defined above for $R_2$ under group (B) or (C) with the further proviso that it is other than hydrogen. Process (a') and (b') may be effected in analogous manner to processes (a) and (b) above.

The splitting off of the amino protecting group according to process (a) may be effected in conventional manner. Preferably the amino protecting group is one capable of being split off hydrolytically, especially under acidic conditions.

$R_{10}$ may be, for example, an acyl group of 2 to 11 carbon atoms, e.g. an aroyl group such as benzoyl, or an alkanoyl group such as acetyl. Alternatively, $R_{10}$ may be alkoxycarbonyl of 2 to 6 carbon atoms or phenoxycarbonyl.

A suitable acid is hydrochloric acid. An inert solvent such as aqueous n-butanol may be present. Suitable temperatures are between 50° and 110° C.

Process (b) may be effected in conventional manner for the alkylation of a secondary amine.

When $R_2^I$ has an hydrogen atom attached to the α-carbon atom thereof, and preferably when $R_2^I$ is methyl, reductive alkylation with the appropriate aldehyde or ketone in the presence of sodium borohydride or sodium dihydrobis-(2-methoxyethoxyethoxy) aluminate may be used.

Suitable alkylation agents include compounds of formula X, $$R_2^I-X \qquad \qquad X$$

wherein
$R_2^I$ is as defined above, and
X is a leaving group.

X may be, for example, halogen such as chlorine, bromine or iodine, or the acid radical of an organic sulphonic acid of up to 10 carbon atoms, e.g. an alkylsulphonyloxy radical such as mesyloxy or an arylsulphonyloxy radical such as tosyloxy. Conveniently an acid binding agent such as triethylamine is present. An inert solvent such as methanol may be present. Suitable temperatures are from 0° to 100° C.

The keto group is preferably protected. It may be in the form of an open chain or cyclic ketal, thiooxoketal or thioketal, the open chain or cyclic portion thereof, for example having from 2 to 4 carbon atoms in the aggregate thereof. Such protected forms may be deprotected in conventional manner.

Process (c) may be effected in conventional manner for the reduction of a cyclohexanone to a cyclohexanol.

The reduction may be effected hydrogenolytically. A suitable catalyst for such a hydrogenation is, for example, platinium. The process may be effected at room temperature, and under normal pressure. Suitable solvents include tetrahydrofuran and ethyl acetate.

The reduction may also be effected with a complex hydride, for example with lithium aluminium hydride, sodium dihydrido-bis(2-methoxyethoxy)aluminate, but preferably sodium borohydride. The reaction may be effected in an inert solvent, e.g. methanol in the case of sodium borohydride. Suitable temperatures may be from 0° to 50° C.

It is to be appreciated that the reduction may not be stereospecific in that two epimers, i.e. a compound wherein the hydroxy group is cis to the 4a-phenyl group [e.g. the (4aRS,6RS,8aRS)isomer] and a compound wherein the hydroxy group is trans to the 4a-phenyl group [e.g. the (4aRS,6SR,8aRS)isomer], may be produced. Such compounds may be separated in conventional manner, e.g. by chromatography on silica-gel.

Process (d) may be effected in conventional manner for a nucleophilic substitution in the presence of an azido anion source, e.g. as described in Example (5b) hereinafter.

The process may be effected in a, preferably polar, inert solvent, such as dimethyl sulphoxide or dimethylformamide. Suitable temperatures may be from 40° to 100° C.

The azido source may be an alkali metal azide such as sodium azide.

$R_{11}$ may be for example an alkanoyloxy group of 1 to 4 carbon atoms, or a radical $R_{14}SO_2O-$, wherein $R_{14}$ is alkyl of 1 to 4 carbon atoms, preferably methyl, or phenyl or p-alkylphenyl of 7 to 11 carbon atoms, especially p-tolyl.

From mechanistic considerations the azido group in the final product will be epimeric to the group $R_{11}$ in the starting material.

Process (e) may be effected in conventional manner for such elimination reactions.

$R_{11}$ may have the preferred values as indicated above. $R_{12}$ when it is a group capable of being split off under the reaction conditions may, for example, be a radical $R_{14}SO_2$, wherein $R_{14}$ is as defined above. The final product in such a case would be a compound of formula If, wherein $R_1$ is hydrogen.

The reaction may be effected in a preferably polar inert solvent, such as dimethyl sulphoxide or dimethylformamide. Suitable temperatures are from 40° to 100° C. The reaction may proceed as a side reaction to process (d) above.

Process (f) may be effected in conventional manner for deprotecting analogous phenolic derivatives.

$R_{13}$ may be, for example, a protecting group capable of being split off by hydrolysis. Such a group is especially preferred when $R_3$ is azido, and may be a group of formula $R_{14}SO_2-$, wherein $R_{14}$ is as defined above. The hydrolysis may be effected in conventional manner for the hydrolysis of similar sulphonic acid esters. For example the reaction may be effected under basic conditions, e.g. in the presence of N-ethyl-diisopropylamine. Suitable temperatures are between 20° and 100° C.

$R_{13}$ may alternatively be a group capable of being split off under ether splitting conditions. Such a group is especially preferred when $R_3$ is other than azido.

The ether splitting may be effected in conventional manner for dealkylation of phenyl alkyl ethers. For example, Lewis acids, such as boron tribromide or aluminium trichloride, or strong mineral acids such as hydrobromic acid or hydroiodic acid may be used. Suitable temperatures are between −20° and +30° C. An inert solvent such as methylene chloride may be present. If desired, when $R_3$ and $R_4$ together are oxygen, the keto group in the starting material of formula IX is in protected form, which is deprotected during the reaction or during the working-up procedure. Thus, the keto group may be protected in the form of an open chain or cyclic ketal, thiooxoketal or thioketal, the open chain or cyclic portion thereof, for example, having from 2 to 4 carbon atoms in the aggregate thereof. Such protected forms may be deprotected in conventional manner. When the deprotecting conditions are acidic, then deprotection will be simultaneous with any dealkylation carried out with a strong mineral acid.

Process (g) may be effected in conventional manner for analogous acylation reactions.

A suitable agent for the introduction of a formyl group may be the mixed anhydride of formic acid and acetic acid. Alkanoyl radicals of 2 to 4 carbon atoms may be introduced using the corresponding acid chloride, bromide or anhydride.

Conveniently a tertiary amine such as pyridine is present. However, when $R_2$ is a radical of formula V, wherein $R_9$ is amino, it may be preferred to use acidic conditions. An inert organic solvent such as toluene may also be present. Suitable temperatures are between 10° and 50° C.

Process (h) may be effected in conventional manner for Wittig reactions. A suitable Wittig salt is methyl triphenylphosphonium bromide. A suitable solvent is dimethylformamide. A suitable temperature is from 10° to 70° C.

The compounds of formula VI may be produced by a process which comprises reacting a compound of formula XI,

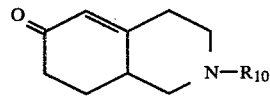

XI wherein $R_{10}$ is as defined above, with a compound of formula XII,

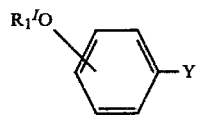

XII wherein
$R_1{}^I$ is as defined above, and
Y is lithium or MgHal, wherein Hal is chlorine, bromine or iodine, in the presence of a cuprous salt, at from −60° to 0° C.

The reaction may be effected in conventional manner for a cuprous-induced 1,4 addition to an α,β-unsaturated ketone.

The cuprous salt used may, for example, be copper (I) iodide, Hydroquinone is preferably present. The reaction is conveniently effected at from −43° to 0° C. The reaction is conveniently effected in an inert solvent, such as tetrahydrofuran.

$R_1{}^I$ is preferably alkyl.

Compounds of formula VIII, wherein $R_{11}$ is $R_{14}SO_2O$—, and $R_{12}$ is $R_1{}^{II}$— or $R_{14}SO_2$—, may be made by reacting a compound of formula Id with $R_{14}SO_2Cl$ in conventional manner.

The configuration of the group —$OSO_2R_{14}$ at $C_6$ in the final product and the hydroxy group at $C_6$ in the starting material will be, in general, the same.

It is to be appreciated that a compound of formula VII is a compound of formula VIII, wherein $R_{12}$ is alkyl or alkanoyl.

Compounds of formula IX, wherein $R_3$ is azido and $R_{13}$ is $R_{14}$—$SO_2$— may be prepared by a nucleophilic substitution with—azide anion in analogous manner to process (d) from a compound of formula VIIIa,

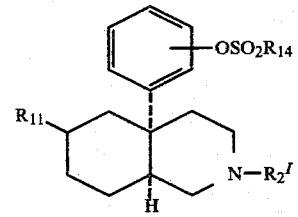

VIIIa wherein
$R_2{}^I$, $R_{11}$ and $R_{14}$ are as defined above.

The starting materials of formula XIII may be obtained as follows:

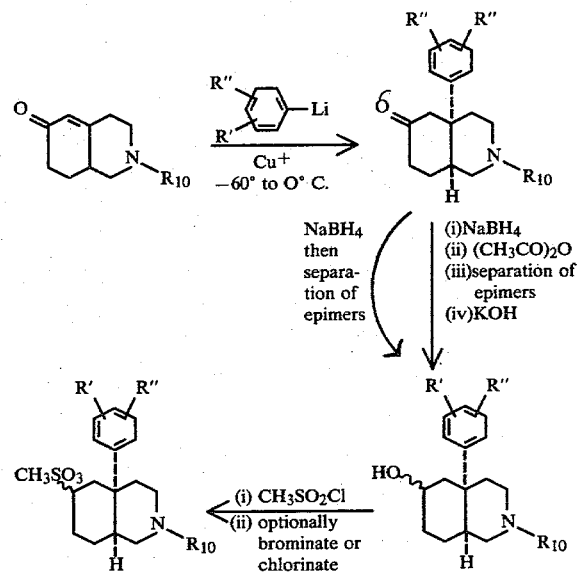

The mesyloxy group of the final product may be displaced by an azido group from an appropriate azide with reversal of the configuration at $C_6$ to yield a compound of formula XIII.

Compounds wherein R′ and/or R″ are chlorine or bromine may be conveniently made by chlorinating or brominating selectively the 4a phenyl ring using conveniently aromatic chlorinating or brominating agents, e.g. pyridinium tribromide.

The configuration of the compounds may be determined on the basis that when the 6-substituents, e.g. azido and hydroxy, is cis to the phenyl ring the compound is more polar on silicagel chromatography, e.g. using $CH_2Cl_2/CH_3OH$ as eluant, than the corresponding 6-epimer.

In so far as the production of any starting material is not particularly described, this is known or may be produced or purified by known processes or in a manner analogous to known processes or to processes herein described.

Free base forms of the compounds of formula I may be converted into acid addition salt forms in conventional manner and vice versa. Suitable acids include hydrochloric acid, maleic acid, oxalic acid, fumaric acid, hydrobromic acid, tartaric acid, malonic acid and di-O,O'-p-toluoyltartaric acid.

The compounds of formula I may exist in racemic or optically active form. The optically active forms may be conveniently made by fractional crystallization of diastereomeric salts. In one convenient method the compounds of formula Ia may be resolved by way of the diastereomeric salts with (+) or (−) tartaric acid and further optically active compounds of formula I may be made therefrom using any of processes (b) to (h) as mentioned above. [after conversion into a starting material for processes (c), (d), (e) (f), (g) and (h)].

Alternatively salts with (+) or (−) di-O,O'-p-toluoyl-tartaric acid, may be used.

In the following examples all temperatures are in degrees Centigrade and are uncorrected.

All compounds obtained are in racemic form unless otherwise stated.

EXAMPLE 1

Octahydro-4a-(3-methoxyphenyl)-cis-6(2H)-isoquinolinone [process (a)]

36.35 g (0.1 mol) of 2-benzoyl-octahydro-4a(3-methoxyphenyl)-cis-6(2H)-isoquinolinone, 100 ml of n-butanol, 33.1 mol of ca. 37% (w/v) aqueous hydrochloric acid (0.4 mol) and 66.9 ml of water are boiled for 40 hours. The mixture is extracted with hexane. The aqueous phase is made basic with aqueous ammonia and extracted with methylene chloride. The organic phases are concentrated by evaporation to yield the title compound which in hydrogen fumarate form has a M.Pt. of 130°.

Separation of optical isomers 25.93 g (100 mmol) of octahydro-4a-(3-methoxyphenyl)-cis-6(2H)-isoquinolinone is dissolved with 15.01 g (100 mmol) of L-(+) tataric acid with slight heating in 40 ml of water and 160 ml of methanol. The mixture is cooled to 0° and the resultant crystals filtered off. After recrystallization of the crystals three times from methanol/water (80:20 v/v) the (+) tartrate having a constant $[\alpha]_D^{20}$ of +28° [1% w/v in H$_2$O] is obtained. The free base is obtained by treatment with methylene chloride/ethanol [80:20 v/v] and aqueous ammonia.

The mother liquors of the above-mentioned crystallizations are treated with ammonia to liberate the free base. After treatment with D(−) tartaric acid as described above the (−) antipode of the tartrate is obtained, $[\alpha]_D^{20} = -28°$ (1% in H$_2$O).

The starting material is obtained as follows:-

278 ml. of 2.2 N butyl lithium solution (612 mmol) are added to a mixture of 600 ml of absolute tetrahydrofuran, 112.2 g (600 mmol) of 3-bromoanisole and 661 mg (6 mmol) of hydroquinone at −65° under nitrogen. The resulting mixture is kept at −50° for 30 minutes, treated with 57.13 g (0.3 mol) of copper (I) iodide, stirred for 1 hour at −43°, and treated with 51.06 g (0.2 mol) of 1,3,4,7,8,8a-hexahydro-2-benzoyl-6(2H)-isoquinolinone. The mixture is allowed to warm to 0° over 2 hours and kept at 0° for 16 hours. 1.2 liters of water and 79.28 g (0.6 mol) of ammonium sulphate are added to the mixture which is then extracted with toluene. The organic extracts are evaporated to yield an oil which is chromatographed on silicagel using ethyl acetate as eluant. The product, 2-benzoyl-octahydro-4a-(3-methoxyphenyl)-cis-6(2H)-iso-quinolinone is obtained as colourless crystals from methanol; M.Pt. 78°.

EXAMPLE 2

Octahydro-4a-(3-methoxyphenyl)-2-methyl-cis-6(2H)-isoquinolinone [process (b)]

25.93 g (0.1 mol) of octahydro-4a-(3-methoxyphenyl)-cis-6(2H)-isoquinolinone (see Example 1), 100 ml of benzene, 11.2 ml (0.2 mol) of ethylene glycol and 8.1 ml (125 mmol) of methanesulphonic acid are boiled for 3 hours in a water separator. The mixture is cooled, made basic with aqueous ammonia and extracted with methylene chloride. The organic phase is evaporated to dryness to yield octahydro-4a-(3-methoxyphenyl)-cis-6(2H)-isoquinolinone ethylene ketal. The ketal is dissolved in 50 ml of absolute methanol, cooled to 0° C., and 13.91 ml (0.1 mol) of triethylamine and 7.46 ml (0.12 mol) of methyl iodide are added thereto. The mixture is kept at 22° for 1 hour. The mixture, containing octahydro-4a-(3-methoxyphenyl)-2-methyl-cis-6(2H)-isoquinolinone ethylene ketal, is mixed with 20 ml of dioxane and concentrated by evaporation. 100 ml of dioxane and 100 ml of 2 N aqueous hydrochloric acid are added to the residual oil. The resultant mixture is stirred for 2 hours at 40°, made basic with aqueous ammonia, and extracted with toluene. The extracts are concentrated by evaporation to yield the title compound as an oil, which is crystallized as the hydrogen fumarate from ethanol.

In analogous manner the following compounds may be made:

(i) 2-allyl-octahydro-4a-(3-methoxyphenyl)-cis-6(2H)-isoquinolinone.
(ii) 2-cyclopropylmethyl-octahydro-4a-(3-methoxyphenyl)-cis-6(2H)-isoquinolinone.
(iii) 2-cyclobutylmethyl-octahydro-4a-(3-methoxyphenyl)-cis-6(2H)-isoquinolinone.
(iv) 2-(o-chlorophenylethyl)-octahydro-4a-(3-methoxyphenyl)-cis-6(2H)-isoquinolinone.

EXAMPLE 3

Octahydro-4a-(3-hydroxyphenyl)-2-methyl-cis-6(2H)-isoquinolinone [process (f)]

To a solution of 28 g of octahydro-4a-(3-methoxyphenyl)-2-methyl-cis-6(2H)-isoquinolinone ethylene ketal obtained as described in Example 2 in 200 ml of methylene chloride at −50° under nitrogen, is added dropwise 28.44 ml (0.3 mol) of boron tribromide in 100 ml of methylene chloride. The mixture is stirred at 0° for 30 minutes, then cooled to −40°, treated with 50 ml of absolute methanol, and concentrated by evaporation. The residue is dissolved in 150 ml of dioxane and 50 ml of water. The resultant mixture is stirred for 1 hour at 40° and partitioned between aqueous ammonia and methylene chloride. The organic phases are then chromatographed on silicagel using a mixture of methylene chloride/methanol/concentrated aqueous ammonia (95:4.5:0.5) as eluant to yield the title compound in amorphous form which crystallizes from isopropyl alcohol; M.Pt. 175°.

In analogous manner there may be obtained:

(i) 2-allyl-octahydro-4a-(3-hydroxyphenyl)-cis-6(2H)-isoquinolinone.
(ii) 2-cyclopropylmethyl-octahydro-4a-(3-hydroxyphenyl)-cis-6(2H)-isoquinolinone.
(iii) 2-cyclobutylmethyl-octahydro-4a-(3-hydroxyphenyl)-cis-6(2H)-isoquinolinone.
(iv) 2-(o-chlorophenethyl)-octahydro-4a-(3-hydroxyphenyl)-cis-6(2H)-isoquinolinone.

EXAMPLE 4

The (4aRS,6SR,8aRS) and (4aRS,6RS,8aRS) epimers of decahydro-6-hydroxy-4a-(3-hydroxyphenyl)-2-methyl-cis-isoquinolinone [process (c)]

To a stirred suspension of 25.93 g (0.1 mol) of octahydro-4a-(3-hydroxyphenyl)-2-methyl-cis-6(2H)-isoquinolinone (see Exampl 3) in 200 ml of methanol at 0°, is added 5.68 g (0.15 mol) of sodium borohydride. The mixture is kept at 22° for 16 hours. The mixture is cooled to 0°, and 50 ml of acetone, 39.6 g (0.2 mol) of ammonium sulphate and 200 ml water are added thereto. The reaction mixture is extracted with a mixture of methylene chloride and ethanol (80/20 v/v). The organic phases, containing a mixture of the two epimeric forms as detected by thin layer chromatography on silicagel, are concentrated by evaporation. The residue is mixed with 19.02 g (0.1 mol) of p-toluenesulphonic acid hydrate and 200 ml of ethanol, and crystallized at 0° to yield the p-toluenesulphonate of the less polar (4aRS,6SR,8aRS) epimer; M.Pt. 253°.

The mother liquor is evaporated and partitioned between aqueous ammonia and a mixture of methylene chloride and ethanol (80:20 v/v). The organic extracts are chromatographed on silicagel using a mixture of methylene chloride/methanol/aqueous ammonia (80:18.2 v/v) yielding the polar, (4aRS,6RS,8aRS), epimer as a colourless amorphous powder which liquifies at about 110°.

In analogous manner the following compounds may be obtained:
(i) (4aRS,6SR,8aRS) and (4aRS,6RS,8aRS) 2-allyl-decahydro-6-hydroxy-4a-(3-hydroxyphenyl)-cis-isoquinoline,
(ii) (4aRS,6SR,8aRS) and (4aRS,6RS,8aRS) 2-cyclopropylmethyl-decahydro-6-hydroxy-4a-(3-hydroxyphenyl)-cis-isoquinoline,
(iii) (4aRS,6SR,8aRS) and (4aRS,6RS,8aRS) 2-cyclobutylmethyl-decahydro-6-hydroxy-4a-(3-hydroxyphenyl)-cis-isoquinoline,
(iv) (4aRS,6SR,8aRS) and (4aRS,6RS,8aRS) 2-(o-chlorophenethyl)-decahydro-6-hydroxy-4a-(3-hydroxyphenyl)-cis-isoquinoline.

EXAMPLE 5

(4aRS,6RS,8aRS) 6-azido-decahydro-4a-(3-hydroxyphenyl)-2-methyl-cis-isoquinoline [process (f)]

(a) 4.336 g (10 mmol) of the p-toluenesulphonate of the (4aRS,6SR,8aRS) decahydro-6-hydroxy-4a-(3-hydroxyphenyl)-2-methyl-cis-isoquinoline obtained in Example 4, 10 ml of absolute pyridine, and 4.29 g (22.5 mmol) of p-toluenesulphonyl chloride are mixed at 0° under nitrogen and stirred for 16 hours at 22°. 20 ml of toluene and 20 ml of 2 N aqueous sodium carbonate solution are added to the mixture, which is then stirred at 22° for 15 minutes and extracted with toluene. The organic phase is concentrated by evaporation to yield the bis-tosylate as an amorphous powder.

(b) The bis-tosylate in 10 ml of absolute dimethyl sulphoxide is mixed with 1.3 g (20 mmol) of sodium azide. The mixture is stirred for 16 hours at 70° under nitrogen, and partitioned between toluene and 2 N aqueous sodium carbonate. The organic phase is concentrated by evaporation to yield (4aRS,6RS,8aRS)-6-azido-decahydro-4a-(3-tosyloxyphenyl)-2-methyl-cis-isoquinoline.

(c) 4 g of (4aRS,6RS,8aRS)-6-azido-decahydro-4a-(3-tosyloxyphenyl)-2-methyl-cis-isoquinoline in 10 ml of 2 N methanolic potassium hydroxide solution is boiled for 1 hour, and then adjusted to a pH 8-10 by the addition of carbon dioxide, after the addition of 20 ml of toluene and 20 ml of water. The organic phases are concentrated by evaporation and the residue is crystallized from isopropanol to yield the title compound as colourless crystals; M.Pt. 198° (decomposition).

In analogous manner there may be obtained:
(i) (4aRS,6RS,8aRS)-2-allyl-6-azido-decahydro-4a-(3-hydroxyphenyl)-cis-isoquinoline; M.Pt. 125° (decomp.),
(ii) (4aRS,6RS,8aRS)-2-cyclopropylmethyl-6-azido-decahydro-4a-(3-hydroxyphenyl)-cis-isoquinoline;
(iii) (4aRS,6RS,8aRS)-2-cyclobutylmethyl-6-azido-decahydro-4a-(3-hydroxyphenyl)-cis-isoquinoline;
(iv) (4aRS,6RS,8aRS)-2-(o-chlorophenethyl)-6-azido-decahydro-4a-(3-hydroxyphenyl)-cis-isoquinoline.

EXAMPLE 6

1,2,3,4,4a,5,8,8a-octahydro-4a-(3-hydroxyphenyl)-2-methyl-cis-isoquinoline, and
1,2,3,4,4a,7,8,8a-octahydro-4a-(3-hydroxyphenyl)-2-methyl-cis-isoquinoline [process (e)]

(4aRS,6SR,8aRS)-decahydro-6-tosyloxy-(3-tosyloxyphenyl)-2-methyl-cis-isoquinoline (obtained in Example 5a) in 10 ml of absolute dimethyl sulphoxide and 1 ml of N-ethyl-diisopropylamine is heated at 70° for 16 hours under nitrogen, and then partitioned between toluene and 2 N aqueous sodium carbonate. The organic phase is concentrated by evaporation and chromatographed on silicagel using acetone/triethylamine (99:1) as eluant yielding initially 1,2,3,4,4a,5,8,8a-octahydro-4a-(3-hydroxyphenyl)-2-methyl-cis-isoquinoline, M.Pt. 159° (from toluene/methylene chloride) and then 1,2,3,4,4a,7,8,8a-octahydro4a-(3-hydroxyphenyl)-2-methyl-cis-isoquinoline, M.Pt. 183° (from toluene/methylene chloride).

EXAMPLE 7

4a-(3-acetoxyphenyl)-octahydro-2-methyl-cis6(2H)-isoquinolinone [process (g)]

3.77 ml (40 mmol) of acetic anhydride are added dropwise to a stirred mixture of 5.19 g (20 mmol) of octahydro-4a-(3-hydroxyphenyl)-2-methyl-cis-6(2H)-isoquinoline (see Example 3), 3.22 ml (40 mmol) of pyridine and 20 ml of toluene at 5°. The mixture is then kept at 22° for 2 hours. 20 ml of water is added to the mixture at 5°, and the mixture is stirred for 30 minutes at 22°. 40 ml of methylene chloride are added. Whilst being stirred, the aqueous phase of the resultant two-phase mixture is adjusted to pH 7 by the addition of 4 g of sodium carbonate. The aqueous phase is then separated and extracted with methylene chloride. The organic phases are washed with water, dried, concentrated by evaporation and dried in a high vacuum. The title compound is obtained as a viscous oil which is crystallized as the hydrogen fumarate from isopropanol; M.Pt. 194° (decomposition).

EXAMPLE 8

Decahydro-4a-(3-hydroxyphenyl)-2-methyl-6-methylene-cis-isoquinoline [process (h)]

3.93 g (11 mmol) of methyl triphenylphosphonium bromide in 100 ml of absolute dimethyl formamide is treated with 1.01 g of a 50% w/w sodium hydride dispersion in oil (21 mmol) under nitrogen. The mixture is stirred for 1 hour at room temperature, and then treated with 2.59 g of octahydro-4a-(3-hydroxyphenyl)-2-methyl-cis-6(2H)-isoquinolinone. The mixture is stirred for 16 hours at 40°, and partitioned between methylene chloride and aqueous ammonium sulphate. Evaporation of the organic phase and chromatographic purification on silicagel gives the title compound.

EXAMPLE 9

In analogous manner to that described in Example 1

(4aRS, 6RS, 8aRS) or (4aRS), 6SR, 8aRS)-6-azido-2-benzoyloxy-decahydro-4a-(3-methoxyphenyl)-cis-isoquinoline is converted into (4aRS, 6RS, 8aRS)-6-azido-decahydro-4a-(3-methoxyphenyl)cis-isoquinoline, or (4aRS, 6SR, 8aRS)-6-azido-decahydro-4a-(3-methoxyphenyl)cis-isoquinoline.

The starting materials are obtained by reducing (4aRS, 6aRS)-2-benzoyl-octahydro-4a-(3-methoxyphenyl)-cis-6-(2H)-isoquinolinone (produced in analogous manner to the example 1 starting material) with sodium borohydride in analogous manner to that disclosed in Example 4 to yield the crude (4aRS, 6SR, 8aRS) and (4aRS, 6RS, 8aRS)-6-hydroxy-decahydro derivatives as a mixture. The mixture is acetylated to yield on chromatography (4aRS, 6SR, 8aRS)-6-acetoxy-2-benzoyl-decahydro-4a-(3-methoxyphenyl)-cis-isoquinoline, m.pt. 133°–135° and (4aRS, 6RS, 8aRS)-6-acetoxy2-benzoyl-decahydro-4a-)3-methoxyphenyl)-cis-isoquinoline m.pt. 124°–125°.

The individual alcohols are then converted into the corresponding methanesulphonates which are then converted into the azido starting materials in analogous manner to Example 5.

EXAMPLE 10

Starting from the two free amines produced in Example 9 and alkylating these in the presence of 35% aqueous formaldehyde in ethanol in the presence of sodium borohydride the following compounds are obtained:

(4aRS, 6RS, 8aRS)-6-azido-decahydro-2-methyl-4a-methyl-4a-(3-methoxyphenyl)-cis-isoquinoline, (4aRS, 6SR, 8aRS)-6-azido-decahydro-2-methyl-4a-(3-methoxyphenyl)-cis-isoquinoline, m.pt. 138°–140° from methylethylketone/ether.

EXAMPLE 11

(4aRS, 6RS, 8aRS)-6-azido-decahydro-4a-(3-methoxyphenyl)-cis-isoquinoline is alkylated by isopropyl iodide in the presence of calcium iodide and N-ethyl diisopropyl amine to yield:

(4aRS, 6RS, 8aRS)-6-azido-decahydro-2-isopropyl-4a-(3-methoxyphenyl)-cis-isoquinoline, m.pt. 192°–180° as hydrochloride from methanol/acetone.

EXAMPLE 12

In analogous manner to that disclosed in example 11 the following (4aRS, 6RS, 8aRS) compounds of formula

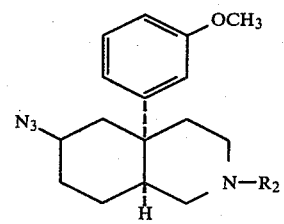

are produced wherein $R_2$ is
(a) $CH_2CH_3$ M.pt. 200°–202° (Hydrochloride)
(b) $CH_2CH_2CH_3$ M.pt. 186°–188° (Hydrochloride)
(c) $CH_2CH(CH_2)_2$ M.pt. 100°–102° (Hydrogenoxalate)
(d) $CH_2CH=C(CH_3)_2$ M.pt. 156°–158° (Hydrogenoxalate)
(e) $CH_2CH_2C_6H_5$ M.pt. 190° (decomp.) (Hydrochloride)
(f) $CH_2$—Cyclopropyl

EXAMPLE 13

In analogous manner to that disclosed in Ex. 8 the following compound is produced: decahydro-4a-(3-methoxyphenyl)-2-methyl-6-methylene-cis-isoquinoline.

EXAMPLE 14

In analogous manner to that disclosed in Example 10 or 11 starting from the corresponding N-desmethyl compound the following compounds of formula

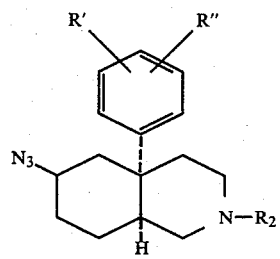

are produced wherein $R_2$ is methyl or isopropyl and

| | R' | R'' | Configuration |
|---|---|---|---|
| (a) | 3-OH | H | (4aRS, 6RS, 8aRS) |
| (b) | H | H | (4aRS, 6RS, 8aRS) |
| (c) | 3-OCH$_3$ | 4Br | (4aRS, 6RS, 8aRS) |
| (d) | 3-CH$_3$ | H | (4aRS, 6RS, 8aRS) |
| (e) | 4-OH | H | (4aRS, 6RS, 8aRS) |
| (f) | 4-OCH$_3$ | H | (4aRS, 6RS, 8aRS) |
| (g) | 2-CF$_3$ | 4n-C$_6$H$_{13}$ | (4aRS, 6RS, 8aRS) |
| (h) | 3-OC$_2$H$_5$ | H | (4aRS, 6RS, 8aRS) |
| (i) | 3-OisoC$_3$H$_7$ | H | (4aRS, 6RS, 8aRS) |
| (j) | 3-OisoC$_3$H$_7$ | H | (4aRS, 6SR, 8aRS) |
| (k) | 3-OH | H | (4aRS, 6SR, 8aRS) |
| (l) | H | H | (4aRS, 6SR, 8aRS) |
| (m) | 3-OCH$_3$ | 4Br | (4aRS, 6SR, 8aRS) |
| (n) | 3-CH$_3$ | H | (4aRS, 6SR, 8aRS) |
| (o) | 4-OH | H | (4aRS, 6SR, 8aRS) |
| (p) | 4-OCH$_3$ | H | (4aRS, 6SR, 8aRS) |
| (q) | 2-CF$_3$ | 4n-C$_6$H$_{13}$ | (4aRS, 6SR, 8aRS) |

-continued

| | R' | R" | Configuration |
|---|---|---|---|
| (r) | 3-OC$_2$H$_5$ | H | (4aRS, 6SR, 8aRS) |

EXAMPLE 15

(4aRS,6SR, 8aRS)-6-azido-decahydro-4a-(3-hydroxyphenyl)-2-methyl-isoquinoline (a) (4aRS, 6RS, 8aRS)-2-benzoyl-decahydro-6-hydroxy4a-(3-hydroxyphenyl)-cis-isoquinoline 218.1 g (0.6 mol) 2-benzoyl-octahydro-4a-(3-methoxyphenyl)-cis-6(2H)-isoquinolinone suspended in 600 ml absolute 2-propanol are boiled and stirred while 6.81 g (180 mmol) of sodium borohydride are added thereto over 15 minutes under a nitrogen atmosphere. The mixture is boiled for a further hour. Under ice-cooling 20 ml acetone are added, and the resultant mixture is partitioned between 600 ml CH$_2$Cl$_2$ and 600 ml water. The organic phase is dried and evaporated to a residue which is pulverised and dried in a high vacuum to leave a colourless powder comprising the epimeric mixture of (4aRS, 6RS, 8aRS)-2-benzoyl-6-hydroxy-4a-(3-methoxyphenyl)isoquinoline and (4-aRS, 6SR, 8aRS)-2-benzoyl-6-hydroxy-4a-(3-methoxyphenyl)-isoquinoline.

The powder is dissolved in 1200 ml absolute CH$_2$Cl$_2$. To this solution, kept at −50° under nitrogen a solution of 125 ml boron tribromide (1.32 mol) in 600 ml absolute CH$_2$Cl$_2$ is added over 1 hour. The stirred mixture is allowed to warm up to 22° and maintained at that temperature for 4 hours. 300 ml CH$_3$OH are then added dropwise at −15°, and 450 ml 25% aqueous ammonia at −5°. 3.6 liters water and 600 ml ethanol are added. The aqueous phase is extracted with methylene chloride. The combined organic phases are dried, evaporated, pulverised and dried in a high vacuum. The residue is stirred for 2 days in 1200 ml acetone/hexane (80:20) at 0° and filtered to separate out the less polar (4aRS, 6SR, 8aRS)-2-benzoyl-6-hydroxy-4a-(3-hydroxyphenyl)isoquinoline. The mother liquor is chromatographed on a column of 1.2 kg silicagel made up using 2.4 liters CH$_2$Cl$_2$ and 30 ml 25% aqueous NH$_3$. On elution with CH$_2$Cl$_2$/CH$_3$OH/25% aqueous NH$_3$ (95:4.5:0.5) the less polar (4aRS, 6SR, 8aRS)-2-benzoyl-6-hydroxy-4a-(3-hydroxyphenyl)isoquinoline is eluted first followed by (4aRS, 6RS, 8aRS)-2-benzoyl-6-hydroxy-4a-(3-hydroxyphenyl)isoquinoline which is crystallized in three parts from acetone at 22°. M.pt. 214°-215°.

(b) (4aRs, 6SR, 8aRS)-6-azido-decahydro-4a-(3-hydroxyphenyl)-cis-isoquinoline 24.6 g (70 mmol) of (4aRS, 6RS, 8aRS)-2-benzoyl-6-hydroxy-4a-(3-hydroxyphenyl)isoquinoline mixed with 70 ml absolute pyridine and 30.03 g (157.5 m mol) p-toluene-sulphonyl chloride are mixed and stirred at 50° for 4 hours under nitrogen. The reaction mixture is then partitioned between 140 ml toluene and 140 ml IM sodium carbonate. The organic phase is dried, evaporated, pulverised and dried in a high vacuum.

The resultant (4aRS, 6RS, 8aRS)-2-benzoyl-decahydro6-tosyloxy-4a-(3-tosyloxyphenyl)-cis-isoquinoline is mixed with 70 ml absolute dimethylsulphoxide and 5.46 g (84 mmol) sodium azide and stirred for 7 hours at 80° under nitrogen. The mixture is then partitioned between 140 ml toluene and 280 ml IM sodium carbonate. The organic phase is dried, evaporated, pulverised and dried again in a high vaccum to give a colourless residue of (4aRS, 6SR, 8aRS)-6-azido-2-benzoyl-decahydro-4a-(3-tosyloxyphenyl)-cis-isoquinoline.

This is hydrolysed by warming the material at 60° in 70 ml isopropanol and 70 ml 2 N aqueous KOH for 24 hours. 140 ml toluene and 140 ml water are added to the mixture. Solid carbon dioxide is added with stirring until the mixture is at pH 8. The organic phase is then evaporated, pulverised and dried in a high vacuum to yield (4aRS, 6SR, 8aRS)-6-azido-2-benzoyl-decahydro-4a-(3-hydroxyphenyl)cis-isoquinoline.

This is then added to 70 ml n-butanol and 70 ml 4 N aqueous HCl and boiled for 32 hours. The acid reaction mixture is extracted twice with hexane. The hexane phase is washed with water. The combined aqueous phases are treated under ice-cooling with 140 ml 5 N aqueous ammonia and extracted with CH$_2$Cl$_2$/C$_2$H$_5$OH. After evaporation of the organic phase the residue is crystallized from 20 ml isopropanol at 0° with stirring to give (4aRS, 6SR, 8aRS)-6-azido-decahydro-4a-(3-hydroxyphenyl)-cis-isoquinoline. M.pt. 222°-224° (decomp).

(c) 4.09 g (15 mmol) (4aRS, 6SR, 8aRS)-6-azido-decahydro4a-(3-hydroxyphenyl)-cis-isoquinoline in 15 ml absolute ethanol and 35% aqueous formaldehyde (189 mmol) are stirred. 2.27 g (60 mmol) sodium borohydride are added with ice-cooling over 40 minutes and the mixture maintained for 4 hours.

7.5 ml further formaldehyde solution are added dropwise. Then 15.9 g ammonium sulphate is added. The mixture is partitioned between 90 ml water and 30 ml CH$_2$Cl$_2$. The organic phase is evaporated. The residue is chromatographed on a 45 g silicagel column made up using 100 ml CH$_2$Cl$_2$ and 0.5 ml 25% aqueous ammonia. The eluant used is CH$_2$Cl$_2$/CH$_3$OH/25% aqueous NH$_3$ (98:1.8:0.2 to 95:4.5:0.5). The title compound is obtained and is crystallized from a mixture of acetone/hexane (2:7). M.pt. 139°-140°.

EXAMPLE 16

(4aRS, 6RS, 8aRS)-6-azido-decahydro-4a-(3-methoxyphenyl)-cis-isoquinoline (4aRS, 6RS, 8aRS)-6-azido-2-benzoyl-decahydro-4a-(3-methoxyphenyl)-cis-isoquinoline in 40 ml n-butanol are treated with 40 ml 4 N HCl. The mixture is stirred at 90° for 72 hours, cooled and extracted with hexane. The aqueous phases are made alkaline with 10% (by weight) Na$_2$CO$_3$ and extracted with CH$_2$Cl$_2$/C$_2$H$_5$OH (8:2). The extracts are evaporated and chromatographed on silicagel using as eluant CH$_2$Cl$_2$: CH$_3$OH: conc. NH$_4$OH (95:4.5:0.5). The title compound is obtained, M.pt. (HCl salt) 113°-115° (from acetone/ether).

The starting material is obtained as follows:

(a) A mixture of 600 ml absolute tetrahydrofuran, 112.2 g 3-bromoanisole and 661 mg hydroquinone are treated under nitrogen at −65° with 278 ml 2.2 N butyl lithium, maintained at −50° for 30 minutes and then treated with 57.13 mg copper (I) iodide, stirred at −43° C. for 30 minutes and then treated with 1, 3, 4, 7, 8, 8a-hexahydro-2-benzoyl-6(2H)isoquinolinone. The mixture is warmed to 0° over 2 hours, maintained at 0° for 16 hours and then worked up to give 2-benzoyl-octahydro-4a-(3-methoxyphenyl)-cis-6(2H)-isoquinolone. M.pt. 78° (from methanol).

(b) 72.6 g of 2-benzoyl-octahydro-4a-(3-methoxyphenyl)-cis6(2H)-isoquinolone in 200 ml CH$_3$OH is reduced at 0° with 2.84 g NaBH$_4$ over 2 hours. 20 ml acetone and 200 ml H₂O are added and the mixture continuously extracted with methylene chloride to give, after working up, a mixture of the 6-hydroxy derivatives as an oil. These were acetylated by 190 ml acetic anhydride in 100 ml pyridine. The mixture is carefully worked up to give an oil. The oil is treated with 80 ml acetone and 50 ml ether and (4aRS, 6SR, 8aRS) -6-acetoxy-2-benzoyldecahydro-4a-(3-methoxyphenyl)-cis-isoquinoline (M.pt. 133°–135°) crystallizes out.

Chromatography of the mother liquor on silicagel and elution with CH₂Cl₂+0.5–1% CH₃OH yields (4aRS, 6RS, 8aRS) -6-acetoxy-2-benzoyl-decahydro-4a-(3-methoxyphenyl)-cisisoquinoline (M.pt. 124°–125° after crystallization from ethyl acetate/ether).

(c) A suspension of 40.8 g (4aRS, 6SR, 8aRS) -6-acetoxy-2-benzoyl-decahydro-4a-(3-methoxyphenyl)-cis-isoquinoline in 200 ml CH₃OH and 50 ml CH₂Cl₂ is stirred and treated with 100 ml 2 N KOH in CH₃OH/H₂O (9:1). After 90 minutes the reaction mixture is evaporated, taken up in CH₂Cl₂/C₂H₅OH (9:1), washed with water, dried and evaporated to yield (4aRS, 6SR, 8aRS) -2-benzoyl-decahydro-6-hydroxy-4a-(3-methoxyphenyl)-cis-isoquinoline as a colourless foam.

(d) 44.3 g of (4aRS, 6SR, 8aRS) -2-benzoyl-decahydro-6-hydroxy4a-(3-methoxyphenyl)-cis-isoquinoline in 300 ml absolute tetrahydrofuran and 60 ml triethylamine are stirred and cooled and treated with 11.4 ml methanesulphonyl chloride in 100 ml absolute tetrahydrofuran. After 1 hour the reaction mixture is poured onto ice and extracted with CH₂Cl₂.

Concentration under a vacuum yields (4aRS, 6SR, 8aRS) 2-benzoyl-decahydro-6-mesyloxy-4a-(3-methoxyphenyl)-cis-isoquinoline. M.pt. 142°–143° (from petroleum ether).

(e) 3.8 g of sodium azide, 12.8 g (4aRS, 6SR, 8aRS) 2-benzoyl-decahydro-6-mesyloxy-4a-(3-methoxyphenyl)-cis-isoquinoline, and 60 ml DMSO are stirred for 6 hours at 80° under nitrogen. The mixture is partitioned between toluene and water. The organic phase is evaporated to yield (4a RS, 6RS, 8aRS)-6-azido-2-benzoyl-decahydro-4a-(3-methoxyphenyl)-cis-isoquinoline.

EXAMPLE 17

(4aRS, 6RS, 8aRS)-6-azido-decahydro-2-methyl-4a-(3-methoxyphenyl)-cis-isoquinoline 28.6 g of (4aRS, 6RS, 8aRS)-6-azido-2-benzoyl-decahydro-4a-(3-methoxyphenyl)-cis-isoquinoline and 100 ml 35% aqueous formaldehyde solution in 300 ml C₂H₅OH are stirred with 19 g NaBH₄. After 30 minutes ice-water is added and the mixture is extracted with CH₂Cl₂. The extracts yield the title compound. M.pt. (hydrogen maleate) 155° from acetone/ether; (HCl salt) from 190° (decomp).

11.88 g of the title compound and 15.96 g di-O,O'-p-toluoyl-L(+)-tartaric acid are dissolved in warm methanol, filtered and allowed to afford crystals at room temperature. The crystals are collected, washed with cold methanol and dried. The crystals are recrystallized four times from methanol. Treatment with 2 N NaOH and CH₂Cl₂ yields the free base of the title compound (−) isomer, $[\alpha]_D^{20} = -24.3°$ (c=0.5 in pyridine) which is converted into the hydrochloride M.pt. 170°–172° $[\alpha]_D^{20} = -50.3°$ (c=0.5 in H₂O).

In analogous manner the (+) isomer of the title compound is obtained by fractional crystallization of the di-O,O'-toluoyl-D(−)-tartaric acid salt. $[\alpha]_D^{20}$ (free base) = +24.1 (c=0.5 in pyridine); (hydrochloride) = +48.6° (c=0.5 in H₂O).

EXAMPLE 18

(4aRS, 6RS, 8aRS)-6-azido-decahydro-2-methyl-4a-(3-methoxyphenyl)-cis-isoquinoline 1.43 g (4aRS, 6RS, 8aRS)-6-azido-decahydro-4a-(3-methoxyphenyl)-cis-isoquinoline in 25 ml acetone and 25 ml CH₃OH as solvent are treated with 0.95 ml N-ethyl-diisopropylamine as condensation agent, 0.91 g potassium iodide and 0.1 ml methyl iodide. The mixture is warmed to 50° under nitrogen. After 20 hours the mixture is worked up to give the title compound, M.pt. (HCl salt) 190° (decomp).

In analogous manner to that described above the following compounds of formula I are produced:

| Ex | R' | R₂ | R₃ | Configuration[1] | M.pt[2] | Production analogous to Example |
|---|---|---|---|---|---|---|
| 19 | 3-OCH₃ | H | H | 6-SR | 138–41°[4] | 16 |
| 20 | 4-OCH₃ | H | H | 6-RS | [5] | 16 |
| 21 | 4-OCH₃ | H | H | 6-SR | [5] | 16 |
| 22 | 3-OCH₃ | 4-Br | H | 6-RS | | |
| 23 | 3-OCH₃ | 4-Br | CH₃ | 6-RS | >240°[3] | 17/18 |
| 24 | 3-OC₂H₅ | H | H | 6-RS | | 1 |
| 25 | 3-OC₂H₅ | H | CH₃ | 6-RS | >184°[3] | 17/18 |
| 26 | 3-O—isoC₃H₇ | H | H | 6-RS | 113–144° | 1 |
| 27 | 3-O—isoC₃H₇ | H | CH₃ | 6-RS | 188–9° | 17/18 |
| 28 | 3-CH₃ | H | H | 6-RS | 212–214° | 1 |
| 29 | 3-CH₃ | H | CH₃ | 6-RS | >180°[3] | 17/18 |
| 30 | 3-CH₃ | H | H | 6-SR | | |
| 31 | 3-CH₃ | H | CH₃ | 6-SR | 185°[3] | 1 |
| 32 | H | H | H | 6-RS | | |
| 33 | H | H | CH₃ | 6-RS | 190°[3] | 17/18 |

[1] 6-RS = (4aRS, 6RS, 8aRS) isomer 6-SR = (4aRS, 6SR, 8aRS) isomer
[2] HCl salt unless otherwise stated
[3] decomposition
[4] hydrogen malonate
[5] hydrogen fumarate mixture of 6RS/SR isomers 188° (decomp)

In analogous manner to that described in Example 7 the following compounds of formula I may be obtained, wherein R₁ is ortho and para nC₃H₇CO, R₃ is N₃, R₄=R₅=R₆=H, and R₂ is:

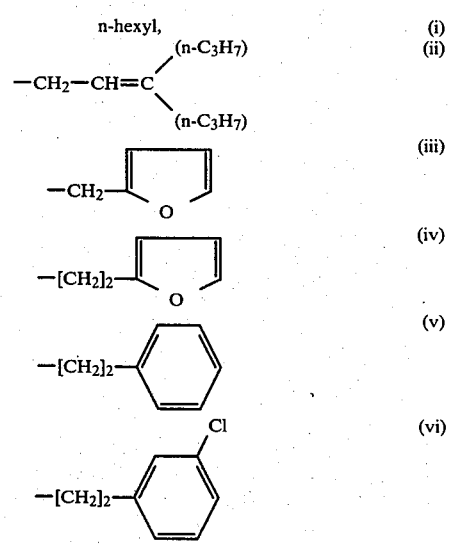

-continued

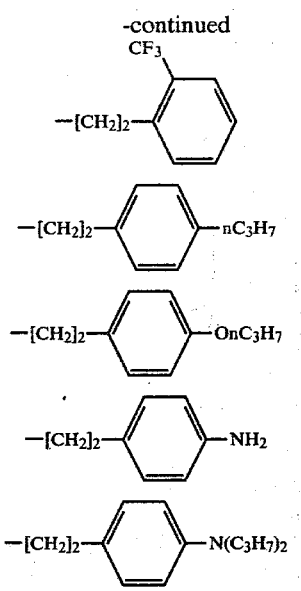

The following compounds of formula

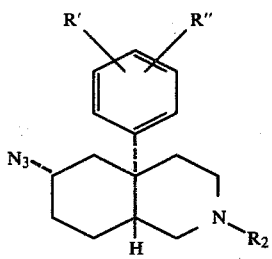

may be made in analogous manner to Example 18.

| Ex | R' | R" | R₂ |
|---|---|---|---|
| (a) | 3-n-C₆H₁₃ | 4-n-C₆H₁₃ | H |
| (b) | 2-CF₃ | 4-CF₃ | H |
| (c) | 2-F | H | H |
| (d) | 2-OC₂H₅ | 4-OC₂H₅ | H |
| (e) | 2-CF₃ | 4-CF₃ | —CH₂—CH═CH(n-C₄H₄)₂ |
| (f) | 3-n-C₆H₁₃ | 4-nC₆H₁₃ | —(CH₂)ₙ—⟨O⟩ n = 1 or 2 |
| (g) | 2-F | H | —(CH₂)₂—⟨⟩—R₆' |
|  |  |  | R₆' = H,Cl,CF₃,OC₂H₅, C₂H₅, NH₂, C₂H₅NH- or (C₂H₅)₂N— |
| (h) | 2-OC₂H₅ | 3-n-C₆H₁₃ | —(CH₂)₂—CH(CH₂)ₘ |
|  |  |  | m = 2,3 or 4 |
| (i) | 3-OC₂H₅ | 5-CF₃ | n-C₆H₁₃ |
| (j) | 2-OC₂H₅ | H | —CH₂—CH═CH₂ |
| (k) | 2-OC₂H₅ | 4-OC₂H₅ | C₂H₅ |

The compounds of formula I are useful as analgesic agents for the treatment of pain, as indicated in standard tests, e.g. in the phenylbenzoquinone writhing test in mice on p.o. administration of from 0.5 to 50 mg/kg of the compounds, and in the tail flick test in mice on s.c. administration from 0.5 to 100 mg/kg of the compounds.

The compounds of formula

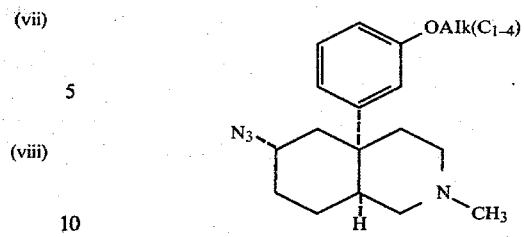

exhibit notable analgesic activity in the above tests as well as notable activity on oral administration in e.g. the arthritic-pain test in the rat over 1 to 5 hours on administration of from 1 to 10 mg/kg p.o. These compounds also appear to be well tolerated in the mouse and rat at doses of from 50 to 100 mg/kg. Furthermore these compounds appear to be exhibit less morphine dependent effects than expected for such compounds as indicated by the following properties:

(i) These compounds do not appear to bind selectively to rat brain opiate receptors. In standard tests for indicating the inhibition of specific $^3$H-naloxone binding to rat brain membranes, e.g. according to the principles of Pert C.B. and Synder S.H., Science 179, 1011–1014 (1973) and Molec, Pharmac. 10, 868–869 (1971), a high concentration of compound, e.g. 1000 to 100,000 nM, was required to inhibit the specific binding of $^3$H-naloxone (1 nM) both in the presence of 100 nM sodium chloride and in the absence of sodium chloride.

(ii) These compounds do not appear to be induce significant dose-dependent jumping behaviour in morphine-dependent mice on administration of from 30 to 100 mg/kg i.p. In one standard test male mice (OFI) strain weighing about 25 g were implanted under light ether anaesthesia with a pellet containing 75 mg morphine base. After recovering, the animals were maintained in groups of 10 with free access to food and water. 6 days after the implantation the mice were judged to be morphine dependent. The compound was then administered and the number of jumps recorded in a 50 minute period thereafter recorded.

(iii) These compounds do not appear to markedly inhibit the withdrawal syndrome in morphine dependent monkeys at a dose of from 1 to 10 mg/kg i.v. One standard test is carried out as follows:

Male rhesus monkeys (2.5–3.4 kg) were kept, each in a metal harness (weight 600 g), in separate, openfronted cubicles (70×70×90 cm) with free access to food and water; and a 12 hour light-dark cycle (6 a.m.–6 p.m. light) maintained. After 7 days acclimatisation to their harnesses and to the cages, the monkeys were anaesthetized with pentothal i.v. and halothane and implanted with a single-lumen silastic catheter into the left jugular vein. The free end of the catheter was then led subcutaneously over the shoulder of each animal and out through a small stab wound made in the skin between the shoulder blades. The monkeys were refitted into their harnesses and connected to a saline-filled cannula coming from the injection pumps. During the 7 day recovery period, all animals received 0.8 ml physiological saline every 30 minutes in order to keep the tip of the cannula free of clots.

Each monkey received programmed injections of morphine (3.2 or 5.6 mg/kg i.v.) at intervals of 4 hours. After several weeks the morphine injections were stopped and two hours after the last morphine injection the compound was administered to the animal. The nature and intensity of the withdrawal syndrome was then recorded.

In the above tests the Example 17 title compound showed especially interesting activity. The (−) form of the Example 17 compound exhibits more interesting activity than the (+) form. This indicates that all optical isomers having the same absolute configuration as the (−) form of the Example 17 compound are the preferred optical isomers.

For this use the dosage will, of course, vary depending on the compound employed, mode of administration and treatment desired. However, in general, satisfactory results are obtained when administered at a daily dosage of from about 0.1 mg to about 100 mg per kg animal body weight, conveniently given in divided doses 2 to 4 times a day or in sustained release form. For the larger mammals, the total daily dosage is in the range from about 20 to about 300 mg, and dosage forms suitable for oral administration comprise from about 5 mg to about 150 mg of the compounds admixed with a solid or liquid pharmaceutical carrier or diluent.

The Example 15 and 17 compounds are the preferred compounds.

The compounds of formula I are futhermore useful as anti-depressant agents, as indicated in standard tests, e.g. in the tetrabenazine catalepsy test in mice on i.p. administration of from 1 to 50 mg/kg of the compounds.

For this use the dosage will, of course, vary depending on the compound employed, mode of administration and treatment desired. However, in general, satisfactory results are obtained when administered at a daily dosage of from about 0.1 mg to about 50 mg per kg animal body weight, conveniently given in divided doses 2 to 4 times a day or in sustained release form. For the larger mammals, the total daily dosage is in the range from about 10 to about 300 mg, and dosage forms suitable for oral administration comprise from about 2 mg to about 150 mg of the compounds admixed with a solid or liquid pharmaceutical carrier or diluent.

The compounds of formula I are furthermore useful as tranquilizing and sleep-inducing agents, as indicated in standard tests, e.g. by an inhibition of the spontaneous locomotor activity of mice on i.p. administration of from 5 to 50 mg/kg of the compounds.

For this use the dosage will, of course, vary depending on the compound employed, mode of administration and treatment desired. However, in general, satisfactory results are obtained when administered at a daily dosage of from about 0.1 mg to about 50 mg per kg animal body weight, conveniently given in divided doses 2 to 4 times a day or in sustained release form. For the larger mammals, the total daily dosage is in the range from about 10 to about 300 mg, and dosage forms suitable for oral administration comprise from about 2 mg to about 150 mg of the compounds admixed with a solid or liquid pharmaceutical carrier or diluent.

The analgesic activity of the compounds is the preferred activity.

The compounds of formula I may be administered in pharmaceutically acceptable acid addition salt form. The present invention also provides a pharmaceutical composition comprising a compound of formula I in free base form or in pharmaceutically acceptable acid addition salt form in association with a pharmaceutical carrier or diluent. Such compositions may be formulated in conventional manner so as to be, for example, a solution or a tablet.

One group of compounds are the following compounds of formula XX wherein
$X_1$, $X_2$ and $X_3$ are chosen from the following significances (i), (ii) and (iii):
(i) $X_1$ and $X_2$, independently, are hydrogen ($C_{1-6}$)alkyl, trifluoromethyl, halogen, or ($C_{1-4}$)alkoxy, and $X_3$ is hydrogen, or
(ii) (a) $X_1$ and $X_2$, independently, are hydrogen, ($C_{1-6}$)alkyl, trifluoromethyl or halogen, or
(b) $X_1$ is ($C_{1-4}$)alkoxy and
$X_2$ is ($C_{1-6}$)alkyl, trifluoromethyl, halogen or ($C_{1-4}$)alkoxy, and
$X_3$ is ($C_{1-6}$)alkyl,
a radical of formula II, $$-CH_2.CH=CX_4X_5 \qquad \text{II}$$

wherein $X_4$ and $X_5$, independently, are hydrogen or ($C_{1-4}$)alkyl,
a radical of formula III, $$-CH_2-CH\underset{(CH_2)_m}{\diagdown}$$

wherein
m is 2, 3 or 4,
a radical of formula IV $$-(CH_2)_n-\text{[furan]} \qquad \text{IV}$$

wherein
n is 1 or 2, or
a radical of formula V $$-(CH_2)_p-\text{[phenyl-}X_6\text{]}$$

wherein
p is 1 or 2 and
$X_6$ is hydrogen, halogen, trifluoromethyl, ($C_{1-4}$)alkoxy, ($C_{1-4}$)alkyl, amino, di[($C_{1-4}$)alkyl]amino ($C_{1-4}$)alkylamino, or
(iii) the azido group is cis to the phenyl group, $X_1$ is ($C_{1-4}$)alkoxy in the meta position
$X_2$ is hydrogen, and
$X_3$ is methyl.

In one group $X_1$, $X_2$ and $X_3$ are chosen from significances (i). In a further group $X_1$, $X_2$ and $X_3$ are chosen from significances (ii) (a). In yet a further group $X_1$, $X_2$ and $X_3$ are chosen from significances (b). In another group $X_1$, $X_2$ and $X_3$ are chosen from significances (iii).

In a first group $X_1$ is hydrogen.
In a 2nd group $X_1$ is alkyl.
In a 3rd group $X_1$ is $CF_3$.
In a 4th group $X_1$ is halogen.
In a 5th group $X_1$ is alkoxy.
In a 6th group $X_2$ is hydrogen.
In a 7th group $X_2$ is alkyl.
In a 8th group $X_2$ is $CF_3$.
In a 9th group $X_2$ is halogen.
In a 10th group $X_2$ is alkoxy.
In a 11th group $X_3$ is alkyl.
In a 12th group $X_3$ is alkenyl as defined above.
In a 13th group $X_3$ is cycloalkylmethyl as defined above.
In a 14th group $X_3$ is furanalkyl as defined above.
In a 15th group $X_3$ is phenylalkyl as defined above.
In a sub-group $X_6$ is other than alkylamino.

We claim:
1. A compound of the formula

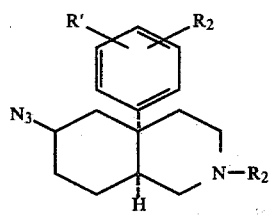

where
R' represents $OR_1$ wherein
$R_1$ is hydrogen, alkyl of 1 to 4 carbon atoms or alkanoyl of 1 to 4 carbon atoms, and
R" is hydrogen, and
$R_2$ is alkyl of 1 to 6 carbon atoms, a radical of formula II

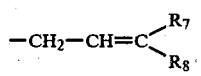

wherein
$R_7$ and $R_8$ independently represent hydrogen or alkyl of 1 to 4 carbon atoms,
a radical of formula III

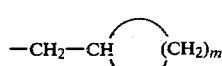

where m is a whole number from 2 to 4, a radical of formula IV

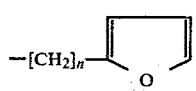

where n is 1 or 2, or a radical of formula V

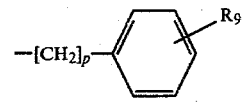

where
P is 1 or 2, and
$R_9$ is hydrogen, halogen, trifluoromethyl, lower alkoxy, lower alkyl, amino or di(lower alkyl) amino,
in free base form or in pharmaceutically acceptable acid addition salt form.

2. The compound of claim 1 which is (4aRS, 6RS, 8aRS)-2-allyl-6-azido-decahydro-4a-(3-hydroxyphenyl)-cis-isoquinoline.

3. A compound of claim 1, wherein $R_1$ is H.
4. A compound of claim 1, wherein $R_1$ is alkyl.
5. A compound of claim 1, wherein $R_1$ is alkanoyl.
6. A compound of claim 1, wherein $R_2$ is alkyl.
7. A compound of claim 1, wherein $R_2$ is a radical of formula II.
8. A compound of claim 1, wherein $R_2$ is a radical of formula III.
9. A compound of claim 1, wherein $R_2$ is a radical of formula IV.
10. A compound of claim 1, wherein $R_2$ is a radical of formula V.

11. The compound of claim 1 which is (4aRS, 6RS, 8aRS)-2-ethyl-6-azido-decahydro-4a-(3-methoxyphenyl)-cis-isoquinoline.

12. The compound of claim 1 which is (4aRS, 6RS, 8aRS)-2-propyl-6-azido-decahydro-4a-(3-methoxyphenyl)-cis-isoquinoline.

13. The compound of claim 1 which is (4aRS, 6RS, 8aRS)-2-isobutyl-6-azido-decahydro-41-(3-methoxyphenyl)-cis-isoquinoline.

14. The compound of claim 1 which is (4aRS, 6RS, 8aRS)-2-(3-methyl-2-butenyl)-6-azido-decahydro-4a-(3-methoxyphenyl)-cis-isoquinoline.

15. The compound of claim 1 which is (4aRS, 6RS, 8aRS)-2-phenethyl-6-azido-decahydro-4a-(3-methoxyphenyl)-cis-isoquinoline.

16. A compound of the formula

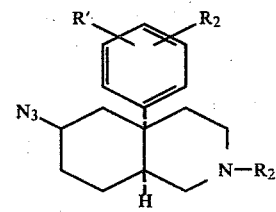

wherein
R' and R" independently represent hydrogen, alkyl of 1 to 6 carbon atoms, trifluoromethyl, halogen or alkoxy of 1 to 4 carbon atoms, and
$R_2$ is alkyl of 1 to 6 carbon atoms,
a radical of the formula II

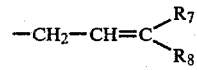

wherein
$R_7$ and $R_8$ independently represent hydrogen or alkyl of 1 to 4 carbon atoms, a radical of the formula III

(III)

wherein m is a whole number from 2 to 4, a radical of the formula IV

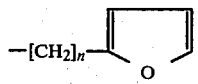
(IV)

wherein n is 1 or 2, or a radical of the formula V

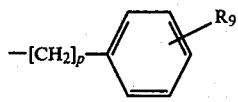
(V)

wherein p is 1 or 2, and $R_9$ is hydrogen, halogen, trifluoromethyl, lower alkoxy, lower alkyl, amino or di(lower alkyl) amino, provided that when R' is alkoxy, R" is other than hydrogen, in free base form or in pharmaceutically acceptable acid addition salt form.

17. A compound of claim 16 wherein R" is hydrogen.

18. A compound of claim 16 wherein R" is other than hydrogen.

19. A compound of the formula

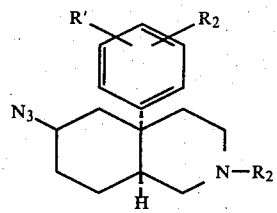

wherein

R' and R" independently represent hydrogen, alkyl of 1 to 6 carbon atoms, trifluoromethyl, halogen or alkoxy of 1 to 4 carbon atoms, and $R_2$ is hydrogen in free base form or in pharmaceutically acceptable acid addition salt form.

20. A compound of formula

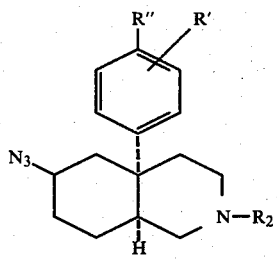

wherein

R' is hydrogen, hydroxy, methoxy, isopropoxy, methyl or trifluoromethyl

R" is in the 4 position and is hydrogen, methoxy, hydroxy, bromine or n—$C_6H_{13}$.

$R_2$ is methyl or isopropyl.

21. The compound of claim 20 which is (4aRS, 6RS, 8aRS)-6-azido-decahydro-2-methyl-4a-(3-methoxyphenyl)-cis-isoquinoline.

22. The compound of claim 20 which is (4aRS, 6RS, 8aRS)-6-azido-decahydro-4a-(3-hydroxyphenyl)-2-methyl-cis-isoquinoline.

23. The compound of claim 20 which is (4aRS, 6SR, 8aRS)-6-azido-decahydro-2-methyl-4a-(3-methoxyphenyl)-cis-isoquinoline.

24. The compound of claim 20 which is (4aRS, 6RS, 8aRS)-6-azido-decahydro-2-isopropyl-4a-(3-methoxyphenyl)-cis-isoquinoline.

* * * * *

UNITED STATES PATENT AND TRADEMARK OFFICE
CERTIFICATE OF CORRECTION

PATENT NO. : 4,301,290
DATED : Nov. 17, 1981
INVENTOR(S) : Paul Pfaffli, Hartmut Hauth It is certified that error appears in the above—identified patent and that said Letters Patent is hereby corrected as shown below:

Col. 25, claim 1, main formula, "$R_2$" in the phenylring should be -- R" --.

Col. 26, claim 16, main formula, "$R_2$" in the phenylring should be -- R" --.

Col. 28, claim 19, main formula, "$R_2$" in the phenylring should be -- R" --.

Col. 26, claim 1, line 8, "P" should be replaced by -- p --.

Signed and Sealed this

Eighth Day of June 1982

|SEAL|

Attest:

GERALD J. MOSSINGHOFF

*Attesting Officer*   *Commissioner of Patents and Trademarks*